United States Patent [19]

Schmid et al.

[11] Patent Number: 5,276,204
[45] Date of Patent: Jan. 4, 1994

[54] FATTY ALCOHOL MIXTURES AND ETHOXYLATES THEREOF SHOWING IMPROVED LOW-TEMPERATURE BEHAVIOR

[75] Inventors: Karl-Heinz Schmid, Mettman; Hans Peter Kubersky, Solingen; Guenter Demmering, Solingen-Graefrath; Alfred Meffert, Monheim, all of Fed. Rep. of Germany

[73] Assignee: Henkel Kommanditgesellschaft auf Aktien, Dusseldorf, Fed. Rep. of Germany

[21] Appl. No.: 965,551

[22] Filed: Oct. 23, 1992

Related U.S. Application Data

[63] Continuation of Ser. No. 690,950, filed as PCT/EP89/01299, Oct. 31, 1989, abandoned.

[30] Foreign Application Priority Data

Nov. 9, 1988 [DE] Fed. Rep. of Germany ....... 3837947

[51] Int. Cl.$^5$ .................. C07C 43/11; C07C 43/15
[52] U.S. Cl. .................. 568/616; 568/622; 568/118; 568/621; 252/351; 252/174.21
[58] Field of Search ............... 568/616, 618, 688, 622, 568/621; 252/351, 174.21

[56] References Cited

U.S. PATENT DOCUMENTS

| | | | |
|---|---|---|---|
| 1,970,578 | 8/1934 | Schoeller et al. | 568/618 |
| 2,094,124 | 4/1937 | Lazur . | |
| 2,226,119 | 12/1940 | De Groote et al. | 568/618 |
| 3,193,586 | 7/1915 | Rittmeister . | |
| 4,233,174 | 11/1980 | Sheridan | 252/174.21 |
| 4,877,556 | 10/1989 | Wilsberg et al. | 252/174.21 |

FOREIGN PATENT DOCUMENTS 1029502 5/1966 United Kingdom .

OTHER PUBLICATIONS

Chem. Abs. 102: 97323t (1985).
Chem Abs 90: 73616y (1979).

*Primary Examiner*—Howard T. Mars
*Attorney, Agent, or Firm*—Ernest G. Szoke; Wayne C. Jaeschke; Real J. Grandmaison

[57] ABSTRACT

Fatty alcohol mixtures $R_{mix}$—OH of natural and, in particular, purely vegetable origin and ethoxylates thereof showing improved low-temperature behavior and corresponding to the general formula $R_{mix}$—O—$(CH_2CH_2O)_x$—H, in which x is a number of 2 to 10 and $R_{mix}$ represents selected mixtures of saturated and olefinically unsaturated fatty alcohol hydrocarbon radicals in the C 6–20 or C 12–20 ranges correspond to specification I for the chain length range $R_{mix}$—=6–20 and to specification II for the chain length range $R_{mix}$—=C 12–20:

| | structurally analogous to | Specification I % by weight | Specification II % by weight |
|---|---|---|---|
| C 6 | caproic acid | 0.1–0.6 | — |
| C 8 | caprylic acid | 2.5–10 | — |
| C 10 | capric acid | 2.5–14 | — |
| C 12 | lauric acid | 37–52 | 39–69 |
| C 14 | myristic acid | 10–20 | 10–27 |
| C 16 | palmitic acid | 6–10 | 6–14 |
| C 18 | stearic acid | 1–5 | 1–7 |
| C 18' | oleic acid | 5–23 | 6–31 |
| C 18" | linoleic acid | 1–4 | 1–6 |
| C 18''' | linolenic acid | 0.1–1 | 0.1–2 |
| C 20 | arachic acid | 0.1–1 | 0.1–2 |

9 Claims, No Drawings

FATTY ALCOHOL MIXTURES AND ETHOXYLATES THEREOF SHOWING IMPROVED LOW-TEMPERATURE BEHAVIOR

This application is a continuation of application Ser. No. 07/690,950, filed as PCT/EP89/01299, Oct. 31, 1989, and now abandoned.

Alkyl and alkylaryl polyglycol ethers as nonionic surfactants have acquired increasing significance over the last decade as ingredients of detergents and cleaning preparations and as constituents of emulsifiers in cosmetic or technical preparations. Starting materials for the synthesis of these nonionic surfactants are alkyl phenols, oxoalcohols by the high-pressure (Roelen process) or low-pressure (Shop process) hydroformylation process, alcohols by the Ziegler process and also fatty alcohols of the type obtained, for example, by hydrogenation of natural oils and fats or from the native fatty acids produced therefrom or methyl esters thereof.

Alkyl polyglycol ethers based on oxoalcohols and on Ziegler and fatty alcohols are assuming increasingly greater significance by virtue of their more favorable ecotoxic properties by comparison with the alkyl phenol polyglycol ethers. Since most industrial emulsifiers are used in liquid formulations, one of the most important requirements for nonionic surfactants has always been a low solidification point. The demand for nonionic surfactants having sufficiently good low-temperature behavior has also increased in recent years above all because liquid formulations have made an entry into product areas where, previously, only powder formulations were known. One example of this is, above all, the field of detergents and cleaning preparations, particularly laundry detergents.

Among the alkyl polyglycol ethers, the ethoxylates of alcohols branched in their basic structure are superior in regard to the favorable low-temperature behavior required to those based on linear alcohols, particularly Ziegler alcohols and fatty alcohols, despite the same carbon chain length of the alkyl moiety and the same number of ethylene oxide units in the molecule. It is known that the solidification point of an alcohol and of the ethoxylate prepared therefrom is lower, the more branched the structure of the alcohol.

Particular applicational significance it attributed above all to alkyl ethoxylates containing on average about 5 to 10 mol ethylene oxide per mol alcohol, the alcohol in this case containing in particular from about 12 to 15 carbon atoms. Compounds of this type are distinguished by particularly good washing, wetting, emulsifying and cleaning power. Compounds of this type based on presently available fatty alcohols of native origin having comparable carbon chain lengths and the same number of ethylene oxide groups in the molecule are inferior to the corresponding compounds based on oxoalcohols in regard to low-temperature behavior. By comparison with the efforts presently being made to overcome this problem, the invention seeks to provide a technically better solution.

Natural raw material sources for a fatty alcohol having the applicationally necessary carbon chain length of C 12 to C 14 described above are, in particular, coconut oil, palm kernel oil and babassu oil. However, the disadvantage of these oils is that the fatty alcohols obtained therefrom, particularly in the case of palm kernel oil and babassu oil, still contain considerable quantities of unwanted C 16/C 18 fractions which lead to unsatisfactory low-temperature behavior of the ethoxylates produced therefrom.

If, for example, an alkyl ethoxylate containing on average 7 mol ethylene oxide per mol alcohol is to be conventionally produced from a coconut oil alcohol having similar low-temperature behavior to the corresponding ethoxylate based on an oxoalcohol having a carbon chain length of C 12 to C 15, the C 16/18 fraction has hitherto had to be removed from the alcohol obtained from coconut oil by fractional distillation. Not only is this expensive on account of the distillation costs involved, the C 16/C 18 alcohol separated from the coconut oil fatty alcohol is identical with the fatty alcohol fractions obtainable from the considerably less expensive talica) accordingly, greatly devalued compared with the coconut oil alcohol. The corresponding loss of material through separation of the C 16/C 18 fraction is approximately 20% by weight in the case of the fatty alcohol mixture from coconut oil and approximately 25% by weight in the case of a fatty alcohol mixture from palm kernel oil.

The problem addressed by the present invention was to provide a method of obtaining fatty alcohol mixtures and ethoxylates comparable in their low-temperature behavior with the corresponding materials based on oxoalcohols, but having the applicationally necessary carbon chain length, from preferably purely vegetable oils and fats without the loss of material just mentioned.

In the production of fatty alcohols or fatty alcohol fractions from fats and/or oils of vegetable origin, the fatty acid mixtures obtained from the vegetable starting materials as fatty acid methyl esters have hitherto been reduced by hydrogenation under process conditions to the corresponding alcohols in which not only is the carboxyl function reduced, the olefinic double bonds in the chain are also largely saturated. Typical examples of the process hitherto used for the production of such fatty alcohol fractions include the treatment of fatty acid methyl esters from coconut oil, palm kernel oil and babassu oil at 200° to 250° C. under hydrogen pressures of 250 to 300 bar over a catalyst consisting of copper and chromium oxide, cf. for example H. Baumann, Angew. Chem. 100 (1988) 50 and U. R. Kreutzer, J. Amer. Oil Chem. Soc. 61 (1984), 343.

The present invention is based on the discovery that fatty alcohols and ethoxylates prepared from these fatty alcohols can be produced with considerably better low-temperature behavior from the same vegetable raw materials providing the partially olefinic structure of these starting materials in the chain is altered as little as possible, the carboxyl function being selectively reduced instead. The fatty alcohol fractions obtained in this way, which are very similar in the composition of the hydrocarbon radicals to the type of vegetable oils used and to the fatty acid mixtures present therein, are distinguished by distinctly improved low-temperature behavior. What is more important, however, is that the above-mentioned ethoxylates having the medium degree of ethoxylation necessary, for example, for reasons of detergency unexpectedly show product properties in regard to low-temperature behavior which at least correspond to those of the hitherto superior alcohol derivatives.

It is known per se that, through the choice of suitable process conditions and, in particular, suitable catalysts, the hydrogenating reduction of unsaturated fatty acids to unsaturated alcohols can be carried out with largely selective conversion of the carboxyl function and with the double-bonds in the chain of the starting compounds intact. For example, oleyl alcohol can be obtained from oleic acid or oleic acid methyl ester where special zinc-containing catalysts are used, cf. for example the already cited literature H. Baumann loc. cit. and U. R. Kreutzer loc, cit.. German patent 25 13 377 and the earlier German patents cited therein, 865 741 and 965 236, are additionally mentioned in this regard. By contrast, the essence of the teaching according to the invention lies in the hitherto unknown realization that reaction products of the described type at least equivalent in their performance level to comparable products based on oxoalcohols can be obtained from the vegetable oils or fats of purely natural origin. Accordingly, in the particular aspect under discussion here, chemistry based on natural renewable raw materials has created an important addition in the context of present requirement profiles.

In a first embodiment, therefore, the present invention relates to fatty alcohol mixtures $R_{mix}$—OH of natural and, in particular, purely vegetable origin and ethoxylates thereof having improved low-temperature behavior and corresponding to the general formula $R_{mix}$—O—$(CH_2CH_2O)_x$—H, in which x is a number of 2 to 10, preferably 3 to 9, and $R_{mix}$ represents selected mixtures of saturated and olefinically unsaturated fatty alcohol hydrocarbon radicals in the C 6-20 or C 12-20 ranges which, for the chain length range $R_{mix}$—=C 6-20, correspond to specification I below and, for the chain length range $R_{mix}$—=C 12-20, to specification II below:

|  | structurally analogous to | % by weight |
|---|---|---|
|  | Specification I |  |
| C 6 | caproic acid | 0.1–0.6 |
| C 8 | caprylic acid | 2.5–10 |
| C 10 | capric acid | 2.5–14 |
| C 12 | lauric acid | 37–52 |
| C 14 | myristic acid | 10–20 |
| C 16 | palmitic acid | 6–10 |
| C 18 | stearic acid | 1–5 |
| C 18' | oleic acid | 5–23 |
| C 18'' | linoleic acid | 1–4 |
| C 18''' | linolenic acid | 0.1–1 |
| C 20 | arachic acid | 0.1–1 |
|  | Specification II |  |
| C 12 | lauric acid | 39–69 |
| C 14 | myristic acid | 10–27 |
| C 16 | palmitic acid | 6–14 |
| C 18 | stearic acid | 1–7 |
| C 18' | oleic acid | 6–31 |
| C 18'' | linoleic acid | 1–6 |
| C 18''' | linolenic acid | 0.1–2 |
| C 20 | arachic acid | 0.1–2 |

In one preferred embodiment of the invention, particular significance is attributed among the fatty alcohol mixtures corresponding to specification I where the ratio of the monoolefinically unsaturated hydrocarbon radical containing 18 C atoms to the sum of the mono- and di-olefinically unsaturated hydrocarbon radicals containing 18 C atoms is greater than 78%.

Preferred fatty alcohol mixtures which correspond to the above specifications can be obtained by selective hydrogenation of corresponding mixtures of fatty acids of natural origin, preferably purely vegetable origin, and by selective hydrogenation of corresponding ester mixtures of such fatty acids. Particularly suitable esters for this selective hydrogenation are corresponding esters with monofunctional alcohols, more especially lower monohydric alcohols containing 1 to 5 C atoms.

It is known that the methyl ester and, to a certain extent, also the butyl ester are particularly important in this regard. The selective hydrogenation is carried out with the natural distribution of the saturated and mono- and polyolefinically unsaturated hydrocarbon radicals in the starting material remaining largely intact. Particularly suitable starting materials of purely vegetable origin are coconut oil, palm kernel oil, babassu oil and rocca fat and the fatty acid and, in particular, corresponding fatty acid methyl ester mixtures obtained therefrom.

Fatty alcohol mixtures corresponding to specification I above still contain the lower fractions from C 6 to C 10 which, because of their odor, can be undesirable for certain applications. Accordingly, the invention encompasses the alcohol mixtures corresponding to specification II above which can be readily obtained from the mixtures corresponding to specification I by separation of the C 6–C 10 fraction. However, both fatty alcohol mixtures and, in particular, the ethoxylates obtained therefrom are distinguished by their considerable content of, in particular, C 16/C 18 components. The content of mono-and polyolefinically unsaturated components in this fraction specified in accordance with the invention nevertheless ensures the desired objective of low-temperature stability comparable with that of oxoalcohols and derivatives thereof without substantial losses of the renewable starting material having to be accepted. The ethoxylates of particular interest in this regard are also entirely satisfactory in their other performance properties.

In another embodiment, the present invention relates to the use of fatty alcohol mixtures $R_{mix}$—OH, in which $R_{mix}$—corresponds to specification I or II above for the production of ethoxylates having improved flow at low temperatures, particularly at room temperature. These ethoxylates correspond to the general formula $R_{mix}$—$(O-CH_2CH_2O)_x$—H, in which $R_{mix}$—is as defined above and x is a number of from 2 to 10 and preferably of 3 to 9.

The ethoxylates are prepared from the fatty alcohol mixtures defined in accordance with the invention in known manner by reaction of the alcohol mixtures with ethylene oxide in the presence of alkaline catalysts or acidic catalysts. Extensive literature is available on this known method of producing above all corresponding nonionic surfactants. Alkaline catalysis is widely used in industrial process, the catalysts used generally being sodium methylate and also sodium hydroxide, sodium, sodium ethylate, potassium hydroxide, etc. Through opening of the ring, the reaction is exothermic. The reaction temperature is in the range, for example, from about 135° to 150° C. The reaction product is then neutralized with inorganic or organic acids, for example with acetic anhydride, phosphoric acid or carbon dioxide. The ethoxylation product formed is not uniform, instead polymer homologs are obtained. The distribution curve differs according to the type of catalyst used. In addition to the typical discontinuous ethoxylation process described herein, there are also continuous processes where the reaction conditions selected can be much more drastic. For example, the ethoxylation reaction may be carried out at 50 to 70 atm and at 250° to 350° C. For literature on this subject, see for example the Article by Dr. W. Wirth in "Tenside, Detergents" 12 (1975) 245-254 and the literature cited therein.

Finally, in another embodiment, the invention relates to the use of ethoxylates of selected fatty alcohol mixtures of natural and preferably purely vegetable origin corresponding to the general formula $R_{mix}$—O—$(CH_2CH_2O)_x$—H, in which $R_{mix}$— corresponds to specification I or II above and x is on average a number of from 2 to 10 and preferably from 3 to 9, as a surfactant component having improved low-temperature behavior. Ethoxylates of the type in question are distinguished in particular at room temperature by their presence as a homogeneous liquid phase, again having good flow properties. Even when surfactant mixtures of the type in question here are solidified by supercooling, such materials soon remelt at room temperature to form a free-flowing, homogeneous liquid phase. Accordingly, the use of materials such as these as a nonionic surfactant component affords considerable advantages in many everyday applications. Not only is handling improved. Hitherto known nonionic surfactants of the type in question based on vegetable fats, particularly with relatively high EO contents within the described range, were endangered by partial solidification of the reaction product in the event of prolonged storage at room temperature. Reaction products such as these, although free-flowing, are understandably difficult to process in batches from a storage container. Before any portions of material can be removed, the contents of the container have to be carefully homogenized in order safely to rule out shifts in the composition of the complex reaction product. The ethoxylates preferred in accordance with the invention are present in the form of a homogeneous liquid phase at room temperature in which separation processes are ruled out from the outset. The storage of unlimited quantities and the removal of material in portions with uniform product properties are thus guaranteed.

In one particular embodiment, the teaching of the invention combines the new measures for improving the low-temperature stability of fatty alcohol ethoxylates of the described type with the teaching of of Applicants' earlier application P 38 02 027.0 U.S. Pat. No. 5,069,817. This earlier application describes a process for the production of alkyl polyglycol ethers having improved low-temperature behavior by reaction of saturated and/or unsaturated, more especially linear, alcohols with ethylene oxide at elevated temperature in the presence of basic alkali metal compounds as catalysts and subsequent neutralization of the alkaline catalyst with organic and/or inorganic acids. The teaching of this earlier application is characterized in that such high concentrations of catalyst are used that a salt is precipitated in the form of an undissolved solid phase in the neutralization step and in that the neutralization step is carried out by precipitation of the salt phase being effected in the presence of finely divided solids dispersed in the reaction product.

The teaching of the earlier application is based on the problem of providing reaction products showing improved low-temperature stability with no deterioration in their other applicational properties by a process which is easy to carry out on an industrial scale. The solution to the problem which the invention addresses is based on the discovery that, by increasing the quantity of basic alkali metal catalysts to a limited extent in the ethoxylation step, it is possible to obtain substantial improvements in the product parameters characterizing low-temperature stability without undesirably impairing the performance properties, such as washing or wetting power, emulsifying power and the like. However, the quantity of basic catalyst has to be increased beyond the limit which characterizes the solubility of the salt formed by neutralization in the ethoxylation product. Accordingly, in the earlier application, this problem is solved by neutralization of the catalyst in the presence of finely divided solids homogeneously distributed throughout the reaction mixture. It has surprisingly been found that incrustations on inner parts of apparatus and/or pipes can be completely prevented by this measure and that, in addition, the reaction product may be filtered without difficulty by conventional methods.

The result of using increased quantities of catalyst in the polyethoxylation step is the production of alkyl polyglycol ether reaction products having a narrow homolog distribution. Narrow homolog distributions generally lead to a reduction in the low-temperature product values, particularly through limitation of the higher-homolog component. The particular embodiment of the present invention under discussion here additionally makes use of this measure according to earlier application P 38 02 027.0 U.S. Pat. No. 5,069,817. Accordingly, the result of the teaching according to the invention are fatty alcohol ethoxylates having further improved and, hence, optimized low-temperature properties.

Particulars of this use of a preferably only slightly increased quantity of alkaline catalysts in the fatty alcohol ethoxylation step can be found in the earlier application P 38 02 027.0 U.S. Pat. No. 5,069,817 cited above. To complete the disclosure of the present invention, the essential elements of that earlier application are summarized in the following.

Organic and/or inorganic filter aids are preferably used as the finely divided solids for precipitating the salt phase in the reaction product, being dispersed in the alkyl polyglycol ether reaction product before the salt phase crystallizes out. The finely divided filter aids are preferably used in quantities of from about 0.3 to 2% by weight and more preferably in quantities of from 0.5 to 1% by weight, based on the alkyl polyglycol ether formed. Other suitable filter aids are, in particular, mixtures of inorganic and organic material, preferably in a ratio of from about 3:1 to 1:3. A suitable inorganic filter aid is, for example, kieselguhr; organic filter aids are, for example, sawdust and/or finely powdered cellulose.

On completion of the ethoxylation step, the reaction product is first partly neutralized, for example to about pH 8, in the presence of the filter aid, subsequently bleached by addition of, in particular, hydrogen peroxide and, only then, fully neutralized to a pH value in the range from about 6.5 to 7.5. The neutralization step and precipitation of the salt phase on the surface of the dispersed filter aid are preferably carried out at a temperature in the range from about 50° to 110° C.

The quantities of basic catalyst used in this process for ethoxylation of the sterically unhindered alcohols are generally at least about 0.5% by weight, expressed as sodium methylate and based on the total mixture of alcohol and ethylene oxide, quantities of from about 0.5 to 1.5% by weight being preferred and quantities in the range from about 0.8 to 1.1% by weight being particularly preferred. The technical teaching is not confined to the use of sodium methylate. Other known basic alkali metal catalysts may also be used in equivalent quantities. Neutralization of the catalyst in the reaction product is carried out with organic and/or inorganic acids, for example gluconic acid, glycolic acid, acetic acid, formic acid, benzoic acid, lactic acid, oxalic acid, citric acid, propionic acid, phosphoric acid, methanesulfonic acid and/or diglycolic acid. Highly corrosive acids, for example sulfuric acid or hydrochloric acid, are of no practical significance.

On completion of neutralization, the ethoxylate in which the filter aid and the salt formed are homogeneously dispersed is pumped to the filtration stage. Filtration may be carried out using both throughflow filters and filter presses and also rotary filters. Ethoxylates of particularly low salt content are obtained when the filtration step, which takes place in a nitrogen atmosphere, is carried out at temperatures above 80° C.

EXAMPLES

For the preparation of the fatty alcohol ethoxylates described in the following Examples and Comparison Examples, the quantities of fatty alcohol, ethylene oxide and catalyst shown in the Examples are reacted in an autoclave for about 3 to 4 hours at 170° to 180° C. under a reaction pressure of 2 to at most 5 bar.

On completion of the alkoxylation reaction, the fatty alcohol ethoxylate is transferred to a stirrer-equipped neutralization vessel and neutralized with lactic acid at 90° C. so that the reaction product has a final pH value (1% of the product in 99% deionized water) in the range from 6.5 to 7.5. In those Examples where the quantity of sodium methylate used for the alkoxylation reaction (based on the total quantity of alcohol and ethylene oxide) exceeds 0.5% by weight, the alkoxylation product is filtered after addition of at most 1% by weight filter aid and subsequent neutralization with tactic acid.

The hydrophilicity of the ethoxylate (cloud point, cloud temperature, turbidimetric titration value) is determined in accordance with DIN 53 917.

COMPARISON EXAMPLE 1

In a continuous hydrogenation reactor, a $C_{12-18}$ fatty acid methyl ester obtained from palm kernel oil by transesterification with methanol and fractionation of the reaction product was reacted with hydrogen at 240° C./250 bar pressure on a copper-containing fixed-bed catalyst to form a mixture of C12-18 fatty alcohol and methanol. After removal of the methanol by distillation, the fatty alcohol had the following characteristics:

| | |
|---|---|
| Hydroxyl value: | 269 |
| Saponification value: | 1.1 |
| Acid value: | 0.02 |
| Iodine value: | 0.12 |
| Solidification point: | 23° C. |

EXAMPLE 1

In a second experiment, the same palm kernel oil fatty acid methyl ester was hydrogenated on a chromium/zinc-containing fixed-bed catalyst in a continuous hydrogenation reactor. The pressure was 250 bar and the temperature 300° C. Under these conditions, the double bonds in the carbon chain of the methyl ester remained intact and a fatty alcohol with the following characteristic data was formed after removal of the methanol also formed by distillation:

| | |
|---|---|
| Hydroxyl value: | 270.5 |

| -continued | |
|---|---|
| Saponification value: | 1.7 |
| Acid value: | 0.02 |
| Iodine value: | 11.7 |
| Solidification point: | 17° C. |

The four coconut oil alcohols "type I to type IV" are used for the following Examples. Types I and III correspond to the definition according to the invention while types II and IV are substantially free from olefinically unsaturated $C_{18}$ alcohols.

| | |
|---|---|
| Coconut oil alcohol (type I) | |
| Hydroxyl value: | 267 |
| Iodine value: | 12 |
| C chain distribution: | |
| C 12 | 53.5 |
| C 14 | 21.8 |
| C 16 | 10.9 |
| C 18 | 4.1 |
| C 18' | 9.7 |
| Coconut oil alcohol (type II) | |
| Hydroxyl value: | 269 |
| Iodine value: | 0.2 |
| C chain distribution: | |
| C 12 | 54.0 |
| C 14 | 22.5 |
| C 16 | 10.1 |
| C 18 | 13.3 |
| C 18' | 0.5 |
| Coconut oil alcohol (type III) | |
| Hydroxyl value: | 266 |
| Iodine value: | 15 |
| C chain distribution: | |
| C 12 | 52.0 |
| C 14 | 21.3 |
| C 16 | 9.0 |
| C 18 | 2.1 |
| C 18' | 15.6 |
| Coconut oil alcohol (type IV) | |
| Hydroxyl value: | 265 |
| Iodine value: | 0.3 |
| C chain distribution: | |
| C 12 | 54.0 |
| C 14 | 17.2 |
| C 16 | 8.5 |
| C 18 | 20.2 |
| C 18' | 0.1 |

EXAMPLE 2

569.9 g coconut oil alcohol (type I) were reacted with 830.1 g ethylene oxide and 12.6 g sodium methylate (30% in methanol, corresponding to 0.27% by weight sodium methylate, based on the total quantity of alcohol and ethylene oxide). An ethoxylate having the following characteristic data was obtained.

| | |
|---|---|
| OH value: | 108 |
| % $H_2O$: | 0.19 |
| Density (70° C.): | 0.9462 |
| Cloud temperature (5 g in 25 g 25% butyl diglycol): | 79° C. |
| % Polyethylene glycol | 2.2, mol. weight 400 |

The product, which corresponds to a fatty alcohol-7EO-adduct, was cooled to −10° C. until it was solid. The product was then stored for 24 hours at 22° C. After this time, the product was liquid.

COMPARISON EXAMPLE 2

565.5 g coconut oil alcohol (type II) were reacted with 834.5 g ethylene oxide and 12.6 g sodium methylate (30% in methanol, corresponding to 0.27% by weight sodium methylate, based on the total quantity of alcohol and ethylene oxide). An ethoxylate having the following characteristic data was obtained.

| | |
|---|---|
| OH value: | 111 |
| % H$_2$O: | 0.16 |
| Density (70° C.): | 0.9468 |
| Cloud temperature (5 g in 25 g 25% butyl diglycol): | 81° C. |
| % Polyethylene glycol | 2.1, mol. weight 800 |

The product, which corresponds to a fatty alcohol-7EO-adduct, was cooled to −10° C. until it was solid. The product was then stored for 1 week at 22° C. After this time, the product was still solid.

EXAMPLE 3

483.8 g coconut oil alcohol (type I) were reacted with 916.2 g ethylene oxide and 7.0 g sodium methylate (30% in methanol, corresponding to 0.154 by weight sodium methylate, based on the total quantity of alcohol and ethylene oxide). An ethoxylate having the following characteristic data was obtained.

| | |
|---|---|
| OH value: | 95 |
| % H$_2$O: | 0.14 |
| Density (70° C.): | 0.9647 |
| Cloud temperature (1% in H$_2$O): | 78° C. |
| % Polyethylene glycol | 2.5, mol. weight 1000 |

The product, which corresponds to a fatty alcohol-9EO-adduct, was cooled to −10° C. until it was solid. The product was then stored for 24 hours at 25° C. After this time, the product was already liquid.

COMPARISON EXAMPLE 3

483.8 g coconut oil alcohol (type II) were reacted with 916.2 g ethylene oxide and 7.0 g sodium methylate (30% in methanol, corresponding to 0.15% by weight sodium methylate, based on the total quantity of alcohol and ethylene oxide). An ethoxylate having the following characteristic data was obtained.

| | |
|---|---|
| OH value: | 92 |
| % H$_2$O: | 0.20 |
| Density (70° C.): | 0.9649 |
| Cloud temperature (1% in H$_2$O): | 79° C. |
| % Polyethylene glycol | 2.3, mol. weight 1100 |

The product, which corresponds to a fatty alcohol-9EO-adduct, was cooled to −10° C. until it was solid. The product was then stored for 1 week at 25° C. After this time, the product was still solid.

EXAMPLE 4

567.5 g coconut oil alcohol (type III) were reacted with 832.5 g ethylene oxide and 12.6 g sodium methylate (30% in methanol, corresponding to 0.27% by weight sodium methylate, based on the total quantity of alcohol and ethylene oxide). An ethoxylate having the following characteristic data was obtained.

| | |
|---|---|
| OH value: | 110 |
| % H$_2$O: | 0.21 |
| Density (70° C.): | 0.9463 |
| Cloud temperature (5 g in 25 g 25% butyl diglycol): | 82° C. |
| % Polyethylene glycol | 2.0, mol. weight 500 |

The product, which corresponds to a fatty alcohol-7EO-adduct, was cooled to −10° C. until it was solid. The product was then stored for 24 hours at 22° C. After this time, the product was liquid.

COMPARISON EXAMPLE 4

567.5 g coconut oil alcohol (type IV) were reacted with 832.5 g ethylene oxide and 12.6 g sodium methylate (30% in methanol, corresponding to 0.27% by weight sodium methylate, based on the total quantity of alcohol and ethylene oxide). An ethoxylate having the following characteristic data was obtained.

| | |
|---|---|
| OH value: | 109 |
| % H$_2$O: | 0.25 |
| Density (70° C.): | 0.9464 |
| Cloud temperature 5 g in 25 g 25% butyl diglycol): | 81° C. |
| % Polyethylene glycol | 2.1, mol. weight 700 |

The product, which corresponds to a fatty alcohol-7EO-adduct, was cooled to −10° C. until it was solid. The product was then stored for 24 hours at 22° C. After this time, the product was still solid.

COMPARISON EXAMPLE 5

A $C_{14-15}$ oxoalcohol containing 7 mol ethylene oxide per mol alcohol was cooled to −10° C. until it was solid. The product was then stored for 4 weeks at 22° C. After this time, the product was still solid.

COMPARISON EXAMPLE 6

A $C_{12-13}$ oxoalcohol containing 7 mol ethylene oxide per mol alcohol was cooled to −10° C. until it was solid. The product was then stored for 24 hours at 22° C. After this time, the product was solid.

We claim:

1. Fatty alcohol ethoxylates having improved low-temperature properties, said fatty alcohol ethoxylates having been prepared by the selective hydrogenation of unsaturated vegetable fats and oil or esters thereof to the corresponding unsaturated alcohols by selective conversion of the carboxyl groups in said vegetable fats and oils or esters thereof to substantially retain the natural distribution of the saturated and mono- and polyolefinically unsaturated hydrocarbon radicals in the starting material, said ethoxylates corresponding to the formula $R_{mix}$—O—(CH$_2$CH$_2$O)$_x$—H in which x is a number of 2 to 10, and $R_{mix}$ represents a mixture of saturated and olefinically unsaturated fatty alcohol hydrocarbon radicals selected from the group consisting of $C_6$ to $C_{20}$ and $C_{12}$ to $C_{20}$ wherein the chain length range $R_{mix}$—=$C_6$–$C_{20}$ corresponds to specification I below and, the chain length range $R_{mix}$—=$C_{12}$–$C_{20}$ corresponds to the specification II below:

| | structurally analogous to | % by weight |
|---|---|---|
| | Specification I | |
| C$_6$ | caproic acid | 0.1–0.6 |

-continued

|  | structurally analogous to | % by weight |
|---|---|---|
| $C_8$ | caprylic acid | 2.5–10 |
| $C_{10}$ | capric acid | 2.5–14 |
| $C_{12}$ | lauric acid | 37–52 |
| $C_{14}$ | myristic acid | 10–20 |
| $C_{16}$ | palmitic acid | 6–10 |
| $C_{18}$ | stearic acid | 1–5 |
| $C_{18'}$ | oleic acid | 5–23 |
| $C_{18''}$ | linoleic acid | 1–4 |
| $C_{18'''}$ | linolenic acid | 0.1–1 |
| $C_{20}$ | arachic acid | 0.1–1 |
| Specification II | | |
| $C_{12}$ | lauric acid | 39–69 |
| $C_{14}$ | myristic acid | 10–27 |
| $C_{16}$ | palmitic acid | 6–14 |
| $C_{18}$ | stearic acid | 1–7 |
| $C_{18'}$ | oleic acid | 6–31 |
| $C_{18''}$ | linoleic acid | 1–6 |
| $C_{18'''}$ | linolenic acid | 0.1–2 |
| $C_{20}$ | arachic acid | 0.1–2 | said ethoxylates having been obtained by reacting the hydrogenated vegetable fats and oils or esters thereof with ethylene oxide at an elevated temperature in the presence of at least about 0.5% by weight of basic alkali metal compound as a catalyst, based on the weight of said hydrogenated vegetable fats and oils or esters thereof and said ethylene oxide, so that a salt of said catalyst is precipitated as an undissolved solid phase during a subsequent neutralization step with acid, said neutralization step having been conducted in the presence of finely-divided solids dispersed in the reaction product, and then separating the neutralized liquid phase from any solids contained therein.

2. Fatty alcohol ethoxylates as in claim 1 wherein in the fatty alcohol mixture corresponding to specification I, the ratio of the monoolefinically unsaturated hydrocarbon radical containing 18 carbon atoms (C18') to the sum of the mono- and diolefinically unsaturated hydrocarbon radicals (C18'+C18") containing 18 carbon atoms is greater than about 78%.

3. Fatty alcohol ethoxylates obtained as in claim 1 wherein said finely-divided solids comprise filter aids.

4. Fatty alcohol ethoxylates obtained as in claim 1 wherein said finely-divided solids are selected from the group consisting of kieselguhr, sawdust, cellulose, and mixtures thereof.

5. Fatty alcohol ethoxylates obtained as in claim 1 wherein said finely-divided solids are present during said neutralization step in a quantity of about 0.3 to about 2% by weight, based on the weight of said fatty alcohol ethoxylates.

6. Fatty alcohol ethoxylates obtained as in claim 1 wherein said neutralization step is stopped at a pH of about 8, the fatty alcohol ethoxylates are bleached by addition of hydrogen peroxide thereto, and the neutralization step is continued until a pH of about 6.5 to about 7.5 is reached in the reaction mixture.

7. Fatty alcohol ethoxylates obtained as in claim 1 wherein said finely-divided solids comprise a mixture of inorganic and organic material.

8. Fatty alcohol ethoxylates obtained as in claim 7 wherein the ratio of inorganic to organic material is from about 3:1 to about 1:3.

9. Fatty alcohol ethoxylates obtained as in claim 1 wherein said neutralization step is carried out with precipitation of a salt of said catalyst on the surface of the dispersed finely-divided solids at a temperature of from about 50° C. to about 110° C.

* * * * *